(12) United States Patent
Subramaniyam

(10) Patent No.: US 11,242,303 B2
(45) Date of Patent: Feb. 8, 2022

(54) COMPOSITION FOR CONTROL AND INHIBITION OF POLYMERIZATION OF MONOMERS, AND METHOD OF USE AND PREPARATION THEREOF

(71) Applicant: Dorf Ketal Chemicals (India) Private Limited, Mumbai (IN)

(72) Inventor: Mahesh Subramaniyam, Mumbai (IN)

(73) Assignee: Dorf Ketal Chemicals (India) Private Limited, Mumbai (IN)

( * ) Notice: Subject to any disclaimer, the term of this patent is extended or adjusted under 35 U.S.C. 154(b) by 0 days.

(21) Appl. No.: 16/491,107

(22) PCT Filed: Mar. 28, 2018

(86) PCT No.: PCT/IB2018/052139
§ 371 (c)(1),
(2) Date: Sep. 4, 2019

(87) PCT Pub. No.: WO2018/185613
PCT Pub. Date: Oct. 11, 2018

(65) Prior Publication Data
US 2020/0010386 A1    Jan. 9, 2020

(30) Foreign Application Priority Data
Apr. 5, 2017 (IN) .............................. 201721012339

(51) Int. Cl.
| C07C 7/20 | (2006.01) |
| C07C 11/04 | (2006.01) |
| C07C 15/46 | (2006.01) |
| C07C 37/01 | (2006.01) |
| C10G 75/04 | (2006.01) |
| C09K 15/26 | (2006.01) |
| C09K 15/28 | (2006.01) |
| C09K 15/04 | (2006.01) |
| C09K 15/24 | (2006.01) |
| C10G 7/10 | (2006.01) |
| C08F 2/00 | (2006.01) |

(52) U.S. Cl.
CPC ............... *C07C 7/20* (2013.01); *C07C 11/04* (2013.01); *C07C 15/46* (2013.01); *C07C 37/01* (2013.01); *C08F 2/002* (2013.01); *C08F 2/005* (2013.01); *C08F 2/007* (2013.01); *C09K 15/04* (2013.01); *C09K 15/24* (2013.01); *C09K 15/26* (2013.01); *C09K 15/28* (2013.01); *C10G 7/10* (2013.01); *C10G 75/04* (2013.01); *B01J 2219/00272* (2013.01); *C08F 2400/00* (2013.01); *C08F 2400/02* (2013.01)

(58) Field of Classification Search
CPC .......... C07C 7/20; C07C 11/04; C07C 15/46; C07C 37/01; C07C 39/08; C08F 2/007; C08F 2/002; C08F 2/005; C08F 2400/00; C08F 2400/02; C10G 75/04; C10G 7/10; C09K 15/26; C09K 15/28; C09K 15/04; C09K 15/24; B01J 2219/00272
See application file for complete search history.

(56) References Cited

U.S. PATENT DOCUMENTS

| 4,628,132 A | 12/1986 | Miller |
| 2013/0098466 A1* | 4/2013 | Manek .................... C10G 29/20 137/13 |
| 2014/0200375 A1 | 7/2014 | Subramaniyam |

FOREIGN PATENT DOCUMENTS

| IN | 201721012339 | 4/2017 |
| JP | 2005213369 A * | 8/2005 ............ C10G 75/04 |
| JP | 2005213369 A | 8/2005 |
| WO | 2018185613 A1 | 10/2018 |

OTHER PUBLICATIONS

Foreign communication from the priority International Application No. PCT/IB2018/052139, International Search Report and Written Opinion, dated Jul. 9, 2018, 10 pages.
Foreign communication from the priority International Application No. PCT/IB2018/052139, International Preliminary Report on Patentability of the International Preliminary Examining Authority, dated Jun. 21, 2019, 12 pages.

* cited by examiner

*Primary Examiner* — Ali Z Fadhel
(74) *Attorney, Agent, or Firm* — Conley Rose, P.C.; Rodney B. Carroll

(57) ABSTRACT

The present invention relates to an additive composition for controlling and inhibiting polymerization of monomers, wherein the composition comprises a combination of (a) a phenol compound comprising catechol compound with (b1) an aliphatic tertiary amine, (b2) oxide treated derivative of the aliphatic tertiary amine, or (b2) a mixture thereof, wherein the aliphatic tertiary amine contains one or more hydroxyl groups in the alkyl chain of the aliphatic tertiary amine. In one embodiment, the present invention also relates to a method for controlling and inhibiting polymerization of monomers by employing the additive composition of the present invention. In another embodiment, the present invention also relates to a method of using the additive composition of the present invention for controlling and inhibiting polymerization of monomers. In another embodiment, the present invention also relates to methods for controlling and inhibiting polymerization of monomers in a primary fractionator (or an ethylene plant), and for operating a primary fractionator, and for reducing fouling and polymer deposits in a primary fractionator, and to extend a run-length of a primary fractionator or of an ethylene plant.

17 Claims, No Drawings

COMPOSITION FOR CONTROL AND INHIBITION OF POLYMERIZATION OF MONOMERS, AND METHOD OF USE AND PREPARATION THEREOF

CROSS REFERENCE TO RELATED APPLICATIONS

This application is a filing under 35 U.S.C. 371 of International Application No. PCT/IB2018/052139 filed Mar. 28, 2018, entitled "Composition for Control and Inhibition of Polymerization of Monomers, and Method of Use and Preparation Thereof," which claims priority to Indian Patent Application No. 201721012339 filed Apr. 5, 2017, which applications are incorporated by reference herein in their entirety.

FIELD OF THE INVENTION

The present invention relates to additive composition for control and inhibition of polymerization of monomers, and method of use and preparation thereof.

Particularly, the present invention relates to additive composition for control and inhibition of polymerization of monomers, wherein the monomers may comprise styrene, indene, di-vinyl benzene, alpha-methyl styrene, and other higher ring compounds or monomers, or derivatives thereof, and method of use and preparation thereof.

More particularly, the present invention relates to additive composition comprising (a) a phenol compound, and (b) one or more aliphatic tertiary amine and/or oxide treated derivative thereof for control and inhibition of polymerization of monomers, wherein the monomers may comprise styrene, indene, di-vinyl benzene, alpha-methyl styrene, and other higher ring compounds or monomers, or derivatives thereof, and method of use and preparation thereof.

BACKGROUND OF THE INVENTION

The polymerization of monomers comprising (or including) styrene indene, di-vinyl benzene, alpha-methyl styrene, and other higher ring compounds or monomers, or derivatives thereof, during processing is a matter of concern, because it causes formation of unwanted polymers and results in problems of fouling and also loss of yield of end product and makes the process un-economical.

Further, the inventor of the present invention has found that formation of the polymerization products of the monomers get deposited at a very rapid rate not only on upper tray surfaces, but also beneath tray surfaces of a primary fractionator, which may also be termed a quench tower, for example, in an ethylene plant, wherein the process would require additional additive, such as, one or more antifoulants.

The inventor of the present invention has further observed that due to the fouling problem, an increase in 'column pressure drop' along with reduction in 'fractionation efficiency' are also experienced.

In the prior art use of inhibitors and retarders, and combination thereof to overcome problem of polymerization of the monomers including styrene has been reported.

The problem of using the inhibitors alone is that these are to be added continuously or at regular intervals, because once they are consumed, the polymerization will re-start.

The problem of using the retarders is that these are not very effective to reduce polymerization of monomers including styrene to a level of substantial inhibition or to the commercially viable level of inhibition.

The prior art discloses compositions for control and inhibition of polymerization of monomers comprising styrene, wherein the composition either consists of a phenol compound, such as catechol compound, for example tertiary butyl catechol (TBC), or comprises a combination of a) phenol compound with b1) quinone methide (QM), particularly 7-aryl-quinone methide; or b2) quinone methide (QM) derivative; or b3) a phenylenediamine; or b4) a hydroxylamine compound; or b5) a mixture thereof, which are required in higher dosage.

The prior art JP 2005 213369 A describes a fouling prevention agent containing (A) an alkanolamine or (A) an alkanolamine and (B) at least one of an N,N-disubstituted hydroxylamine compound, 1,4-dihydroxyanthraquinone (DHAQ), and a phenolic compound. The prior art US 2014/200375 A1 describes an additive composition for control and inhibition of polymerization of styrene consisting of combination of amine and quinone methide. The prior art U.S. Pat. No. 4,628,132 describes a composition comprising a combination of dialkyl amine, dialkylhydroxylamine, and an alkali metal salt of a tertiary-alkylcatechol.

Need of the Invention

Therefore, there is still a need of an additive composition which is not only suitable for substantial control and inhibition of polymerization of monomers, wherein the monomers may comprise styrene, indene, di-vinyl benzene, alpha-methyl styrene, and other higher ring compounds or monomers, or derivatives thereof, but is also required in comparatively low dosage, or at least, relatively requires low dosage of the phenol compound to achieve same or better polymerization inhibition efficiency.

Therefore, there is also a need of an additive composition which (i) can avoid formation of polymerization products of the monomers, and hence, (ii) can avoid deposition of polymerization products of the monomers in a primary fractionator, or a quench tower, and thereby (iii) result in increased efficiency of the ethylene plant by avoiding fouling, and/or (iv) extend a run-length of the primary fractionator or of the ethylene plant.

Therefore, there is also a need of an additive composition which (v) can avoid fouling problems, and hence (vi) can avoid an increase in "column pressure drop" and (vii) can avoid reduction in "fractionation efficiency".

Problem to be Solved by the Invention

Therefore, the present invention aims at providing a solution to above-described existing industrial problems by providing an additive composition which is found to be suitable for controlling and inhibiting polymerization of monomers, wherein the monomers may comprise styrene, indene, di-vinyl benzene, alpha-methyl styrene, and other higher ring compounds or monomers, or derivatives thereof, and is also required in comparatively low dosage, or at least relatively requires low dosage of the phenol compound to achieve same or better polymerization inhibition efficiency.

Therefore, the present invention also aims at providing a solution to above-described existing industrial problems of the primary fractionator, that is, to provide an additive composition which (i) would avoid formation of polymerization products of the monomers, and hence, (ii) would avoid deposition of polymerization products of the monomers in the primary fractionator, or the quench tower, and thereby (iii) would result in increased efficiency of the ethylene plant by avoiding fouling, and/or (iv) extend a run-length of the primary fractionator or of the ethylene plant.

Therefore, the present invention also aims at providing a solution to above-described existing industrial problems of the primary fractionator, that is, to provide an additive composition which (v) would avoid fouling problems, and hence (vi) would avoid an increase in 'column pressure drop' and (vii) would avoid reduction in 'fractionation efficiency'.

Objects of the Invention

Accordingly, the main object of present invention is to provide an additive composition which is suitable for controlling and inhibiting polymerization of monomers, wherein the monomers may comprise styrene, indene, di-vinyl benzene, alpha-methyl styrene, and other higher ring compounds or monomers, or derivatives thereof, and is required in comparatively low dosage as compared to dosage of prior art additive or its individual components for achieving the same or better level of inhibition of polymerization of the monomers.

Accordingly, the other object of the present invention is to provide an additive composition which is suitable (i) for avoiding formation of polymerization products of the monomers, and hence, (ii) for avoiding deposition of polymerization products of the monomers in the primary fractionator, or the quench tower, and thereby (iii) to result in increased efficiency of the ethylene plant by avoiding fouling, and/or (iv) extend a run-length of the primary fractionator or of the ethylene plant.

Accordingly, the still another object of the present invention is to provide an additive composition which is suitable (v) to overcome the fouling problems, and hence (vi) to avoid an increase in "column pressure drop" and (vii) to avoid reduction in "fractionation efficiency".

Other objects and advantages of present invention will become more apparent from the following description when read in conjunction with examples, which are not intended to limit scope of present invention.

DETAILED DESCRIPTION OF THE INVENTION

As discussed herein, it is known that while manufacturing lighter hydrocarbon products such as ethylene, heavier hydrocarbons such as naphtha, condensate or diesel oil are cracked in pyrolysis heaters at higher temperatures, generally at a temperature of about 850° C. and form mixtures of smaller molecules including, but not limited to, ethylene, propylene, and butadiene. Such mixtures, commonly termed as cracked gases, are cooled and compressed in various stages of the ethylene plant until they are separated in the fractionation section of the ethylene plant.

During primary heat recovery, the cracked gases pass through and are cooled by a series of heat exchangers, also termed transfer line exchangers, before being quenched with an oil, preferably an heavy oil. The heavy oil, which is commonly known as quench oil, pyrolysis fuel oil or bottoms quench oil, accumulates in the bottom section of the primary fractionator. The primary fractionator contains varying components of fuel oil species ranging from the bottom section of the column to the beginning of what is called the rectification section of the column.

The rectification section of the column is prone to severe fouling problems caused due to presence of various monomers, such as styrene, indene, di-vinyl benzene, alpha-methyl styrene, indene derivatives, and other higher ring compounds/monomers or derivatives thereof, and polymers thereof.

The polymerization products of the said monomers get deposited at a very rapid rate not only on upper tray surfaces, but also beneath tray surfaces. Due to this fouling problem, an increase in 'column pressure drop' along with reduction in 'fractionation efficiency' are experienced.

Therefore, the quality of the gasoline condensing in the quench tower and also the quality of the fuel oil made from the system are negatively affected.

Typically, the problem of fouling in the rectification section is also accompanied by poor viscosity control in the bottom section of the quench tower due to improper operations of the primary fractionator.

Further, the deposition of the fouling substances, commonly known as polymers, obstructs the vapor and liquid flow inside the fractionator and due to the reduced surface area available, the environment is also conducive to increased froth/foam generation in the column.

As the fouling continues to occur, the polymers deposit also continues to occur inside the column trays thus resulting in forcing the plant operators to reduce unit feed rates significantly and, ultimately, to shut down the plant for cleaning and/or maintaining the primary fractionator.

With aim to overcome above-described problems of prior art and to achieve above-described objects of the invention, the inventor has found that when (a) a phenol compound comprising catechol compound is combined with (b1) an aliphatic tertiary amine and/or (b2) oxide treated derivative thereof, preferably with aliphatic tertiary amine having one or more hydroxyl groups in the alkyl chain of said aliphatic tertiary amine, the polymerization inhibition efficiency of the phenol compound comprising catechol compound surprisingly and unexpectedly increases.

The prior art does not disclose composition for control and inhibition of polymerization of monomers, wherein the monomers may comprise styrene, indene, di-vinyl benzene, alpha-methyl styrene, and other higher ring compounds or monomers, or derivatives thereof to overcome above discussed existing problems of the industry particularly the above-discussed problems of formation of deposits and fouling in the primary fractionator, wherein the composition comprises a combination of:

(a) a phenol compound comprising catechol compound; and (b1) an aliphatic tertiary amine and/or (b2) oxide treated derivative thereof, preferably an aliphatic tertiary amine having one or more hydroxyl groups in the alkyl chain of said aliphatic tertiary amine;

with aim to increase polymerization inhibition efficiency of the phenol compound including catechol compound and/or to reduce amount of the phenol compound including catechol compound for controlling and inhibiting polymerization of the monomers.

Therefore, the present invention provides a composition which has been found to be suitable in reducing the formation of polymers of the monomers, and hence, has also been found to be suitable in preventing the fouling in the primary fractionator or ethylene plant, and thereby, to extend a run-length of the primary fractionator or of the ethylene plant.

Accordingly, in one embodiment, the present invention provides an additive composition for control and inhibition of polymerization of monomers, wherein the composition comprises a combination of:

(a) a phenol compound comprising catechol compound; and (b) an aliphatic tertiary amine, oxide treated derivative of the aliphatic tertiary amine, or a mixture thereof.

Accordingly, in one of the preferred embodiments, the present invention provides an additive composition for control and inhibition of polymerization of monomers, wherein the composition comprises a combination of:

(a) a phenol compound comprising catechol compound; and (b) an aliphatic tertiary amine, oxide treated derivative of the aliphatic tertiary amine, or a mixture thereof, wherein the aliphatic tertiary amine contains (or has) one or more hydroxyl groups in the alkyl chain of the aliphatic tertiary amine.

In accordance with one of the preferred embodiments of the present invention, the aliphatic tertiary amine contains three or more hydroxyl groups in the alkyl chain of the aliphatic tertiary amine.

In accordance with one of the preferred embodiments of the present invention, the aliphatic tertiary amine comprises tri-isopropanol amine (TIPA).

In accordance with one of the preferred embodiments of the present invention, the oxide treated derivative of the aliphatic tertiary amine comprises:

(i) ethyl oxide treated derivative of tri-isopropanol amine (EO-TIPA);

(ii) propyl oxide treated derivative of tri-isopropanol amine (PO-TIPA); or (iii) a mixture thereof.

In accordance with one of the preferred embodiments of the present invention, the phenol compound comprises a catechol compound.

In accordance with one of the preferred embodiments of the present invention, the catechol compound comprises a tertiary butyl catechol (TBC).

In accordance with one of the preferred embodiments of the present invention, the tertiary butyl catechol (TBC) may be selected from the group comprising 4-tert-butyl catechol; 3,5-di-tert-butylcatechol; or a mixture thereof.

It may be noted that it is understood from the present description that the present invention aims at reducing the amount of TBC (the prior art additive) in the present compositions. Therefore, the TBC is a primary component of the present composition, and the TIPA, the EO-TIPA or the PO-TIPA is the additive component of the present composition, and it is the additive component which is added to the primary component, or say, to the composition comprising or consisting of TBC. Therefore, generally, it is the primary component of the present invention which is present in a major percent by weight amount and it is the additive component of the present invention which is present in a minor percent by weight amount. However, one of an ordinary skill in the art may use the present composition in reverse order.

In accordance with the present invention, the monomers comprising or including styrene may be referred to as monomers or a monomer stream, which are intended to include or comprise but not limited to styrene.

In accordance with one of the embodiments of the present invention, the phenol compound and the aliphatic tertiary amine or the oxide treated derivative thereof may be taken in a weight percent ratio varying from about 99.99:0.01 to about 0.01:99.99.

In accordance with one of the preferred embodiments of the present invention, the phenol compound and the aliphatic tertiary amine or the oxide treated derivative thereof may be taken in a weight percent ratio varying from about 90:10 to about 10:90.

In accordance with another embodiment of the present invention, the phenol compound and the aliphatic tertiary amine or the oxide treated derivative thereof may be taken in a weight percent ratio varying from about 80:20 to about 20:80.

In accordance with still another embodiment of the present invention, the phenol compound and the aliphatic tertiary amine or the oxide treated derivative thereof may be taken in a weight percent ratio varying from about 70:30 to about 30:70.

In accordance with yet another embodiment of the present invention, the phenol compound and the aliphatic tertiary amine or the oxide treated derivative thereof may be taken in a weight percent ratio varying from about 60:40 to about 40:60.

In accordance with yet another embodiment of the present invention, the phenol compound and the aliphatic tertiary amine or the oxide treated derivative thereof may be taken in a weight percent ratio of about 50:50.

In accordance with one of the embodiments of the present invention, about 0.01 to about 5000 ppm of the present composition may be used based on weight of the reacting material in polymerization of monomers.

In accordance with another embodiment of the present invention, about 0.20 to about 5000 ppm of the present composition may be used based on weight of the reacting material in polymerization of monomers.

In accordance with still another embodiment of the present invention, about 0.50 to about 5000 ppm of the present composition may be used based on weight of the reacting material in polymerization of monomers.

In accordance with yet another embodiment of the present invention, about 1.0 to about 5000 ppm of the present composition may be used based on weight of the reacting material in polymerization of monomers.

In accordance with yet another embodiment of the present invention, about 5.0 to about 5000 ppm of the present composition may be used based on weight of the reacting material in polymerization of monomers.

In accordance with yet another embodiment of the present invention, about 10.0 to about 5000 ppm of the present composition may be used based on weight of the reacting material in polymerization of monomers.

In accordance with one of the embodiments of the present invention, the additive composition of the present invention may be used or employed at a temperature range varying from about 60° C. to about 180° C., or preferably at a temperature range varying from about 80° C. to about 150° C.

In one embodiment, the present invention relates to a method for controlling and inhibiting polymerization of monomers, wherein the method comprises a step of treating a monomer stream with the additive composition of the present invention.

In another embodiment, the present invention also relates to a method of using the additive composition of the present invention for controlling and inhibiting polymerization of monomers, wherein the method comprises a step of using the additive composition of the present invention in a monomer stream.

It may be noted that the present composition may be used for controlling and inhibition of polymerization of monomers of any composition.

In one of the exemplary embodiments, the present composition is used for controlling and inhibition of polymerization of monomers, wherein the monomers may comprise styrene, indene, di-vinyl benzene, alpha-methyl styrene, and other higher ring compounds or monomers, or derivatives thereof.

In another exemplary embodiment, the present composition is used for controlling and inhibiting polymerization of the monomers in the primary fractionator or the ethylene plant.

Accordingly, in still another embodiment, the present invention also relates to a method for controlling and inhibiting polymerization of monomers in a primary fractionator (or an ethylene plant), wherein the method comprises a step of treating a monomer stream with the additive composition of the present invention.

Accordingly, in yet another embodiment, the present invention also relates to a method for operating a primary fractionator by controlling and inhibiting polymerization of monomers in the primary fractionator (or an ethylene plant), wherein the method comprises a step of using the additive composition of the present invention in a monomer stream.

Accordingly, in yet another embodiment, the present invention also relates to a method for reducing fouling and polymer deposits in a primary fractionator by controlling and inhibiting polymerization of monomers in the primary fractionator (or an ethylene plant), wherein the method comprises a step of treating a monomer stream with the additive composition of the present invention.

Accordingly, in yet another embodiment, the present invention also relates to a method to extend a run-length of a primary fractionator or of an ethylene plant by reducing fouling and polymer deposits in the primary fractionator by controlling and inhibiting polymerization of monomers in the primary fractionator (or an ethylene plant), wherein the method comprises a step of treating a monomer stream with the additive composition of the present invention.

It may also be noted that 'in percent ratio' means 'in weight percent ratio' or 'in percent ratio by weight' unless specifically otherwise provided.

It may also be noted that the term 'about' is intended to include experimentally permissible errors in the field of the present invention.

EXAMPLES

The present invention is now further illustrated with the help of accompanying examples, which are not intended to limit its scope.

Example—I

The pyrolysis gasoline sample was taken in a tube with provision for nitrogen gas purging and the sample was treated at temperatures of about 90° C., about 120° C. and about 150° C. for about 2 hrs. and the polymer formed was separated by methanol precipitation and the percent polymerization in blank (without an additive), comparative sample (with 100 ppm additive consisting of TBC) and the invention sample (with 100 ppm of additive comprising TBC and TIPA in 40:10 weight percent ratio) was measured and has been presented in Table—I.

It may be noted that as per the present invention and as described herein, the TIPA, the EO-TIPA and the PO-TIPA are the additive components of the present composition, and it is the additive component which is added to the primary component, or say, to the composition comprising or consisting of TBC. Therefore, as per the present examples, it is 10% by wt. of the TIPA which is mixed with 40% by wt. of the TBC to arrive at the invention composition of these examples.

TABLE I

| Additive | Expt. | | | | | |
|---|---|---|---|---|---|---|
| | 90° C. | | 120° C. | | 150° C. | |
| | % Polymer by OD | % Polymer by methanol | % Polymer by OD | % Polymer by methanol | % Polymer by OD | % Polymer by methanol |
| Blank | 0.15 | Nil | 1.62 | 0.18 | 3.15 | 1.21 |
| TBC (Comparative Example) | 0.47 | 0.18 | 0.93 | 0.11 | 2.50 | 0.93 |
| TBC + TIPA (Present Invention) | 0.42 | 0.10 | 0.48 | 0.07 | 1.95 | 0.43 |

Example—II

The pyrolysis gasoline sample was taken in a tube and this time without nitrogen gas purging and the sample was treated at temperatures of 120° C. and 150° C. for 2 hrs. and the polymer formed was separated by methanol precipitation and the percent polymerization in blank (without an additive), comparative sample (with 100 ppm additive consisting of TBC) and the invention sample (with 100 ppm of additive comprising TBC and TIPA in 40:10 weight percent ratio) was measured and has been presented in Table—II.

TABLE II

| Additive | Expt. | | | |
|---|---|---|---|---|
| | 120° C. | | 150° C. | |
| | % Polymer by OD | % Polymer by methanol | % Polymer by OD | % Polymer by methanol |
| Blank | 1.46 | 0.13 | 3.05 | 1.14 |
| TBC | 0.82 | 0.09 | 2.34 | 0.86 |

TABLE II-continued

| | Expt. | | | |
|---|---|---|---|---|
| | 120° C. | | 150° C. | |
| Additive | % Polymer by OD | % Polymer by methanol | % Polymer by OD | % Polymer by methanol |
| (Comparative Example) TBC + TIPA (Present Invention) | 0.43 | 0.04 | 1.80 | 0.41 |

The above experiments confirm surprising, unexpected and synergistic effects of the presently provided compositions, because the efficiency of the phenol compound to control and inhibition of polymerization of monomers has increased on combining it with an aliphatic tertiary amine, and/or oxide treated derivative thereof.

The above findings also confirm that compositions of present invention have technical advantages and surprising effects over the prior art additives and compositions, because the efficiency of the phenol compound to control and inhibition of polymerization of monomers has increased on combining it with an aliphatic tertiary amine, and/or oxide treated derivative thereof.

The invention claimed is:

1. An additive composition for control and inhibition of polymerization of pyrolysis gasoline by controlling and inhibiting formation of deposits and fouling in the primary fractionator, wherein the composition consists of a combination of:
   (a) a phenol compound comprising a catechol compound; and
   (b) an oxide treated derivative of the aliphatic tertiary amine consisting of:
      (i) ethyl oxide treated derivative of tri-isopropanol amine (EO-TIPA);
      (ii) propyl oxide treated derivative of tri-isopropanol amine (PO-TIPA); or
      (iii) a mixture thereof.

2. The additive composition as claimed in claim 1, wherein the catechol compound comprises a tertiary butyl catechol (TBC).

3. The additive composition as claimed in claim 2, wherein the tertiary butyl catechol (TBC) comprises 4-tert-butyl catechol; 3,5-di-tert-butyl catechol; or a mixture thereof.

4. A method for controlling and inhibiting polymerization of pyrolysis gasoline, wherein the method comprises a step of treating the pyrolysis gasoline with the additive composition as claimed in claim 2.

5. A method of using the additive composition as claimed in claim 2 for controlling and inhibiting polymerization of pyrolysis gasoline, wherein the method comprises a step of treating the additive composition as claimed in claim 2 with the pyrolysis gasoline.

6. The method of using as claimed in claim 5, wherein the additive composition is added at a temperature range varying from about 60° C. to about 180° C.

7. A method for operating a primary fractionator by controlling and inhibiting polymerization of pyrolysis gasoline in the primary fractionator or an ethylene plant, wherein the method comprises treating the additive composition as claimed in claim 2 with the pyrolysis gasoline in the primary fractionator or an ethylene plant.

8. The method for operating as claimed in claim 7, wherein the additive composition is added at a temperature range varying from about 60° C. to about 180° C.

9. A method for reducing fouling and polymer deposits in a primary fractionator by controlling and inhibiting polymerization of pyrolysis gasoline in the primary fractionator, wherein the method comprises a step of treating the pyrolysis gasoline with the additive composition as claimed in claim 2.

10. A method to extend a run-length of a primary fractionator or of an ethylene plant by reducing fouling and polymer deposits in the primary fractionator by controlling and inhibiting polymerization of pyrolysis gasoline in the primary fractionator or an ethylene plant, wherein the method comprises a step of treating the pyrolysis gasoline with the additive composition as claimed in claim 2.

11. A method for controlling and inhibiting polymerization of pyrolysis gasoline, wherein the method comprises a step of treating the pyrolysis gasoline with the additive composition as claimed in claim 1.

12. A method of using the additive composition as claimed in claim 1 for controlling and inhibiting polymerization of pyrolysis gasoline, wherein the method comprises a step of treating the additive composition as claimed in claim 1 with the pyrolysis gasoline.

13. The method of using as claimed in claim 12, wherein the additive composition is employed at a temperature range varying from about 60° C. to about 180° C.

14. A method for operating a primary fractionator by controlling and inhibiting polymerization of pyrolysis gasoline in the primary fractionator, wherein the method comprises treating the additive composition as claimed in claim 1 with the pyrolysis gasoline in the primary fractionator or an ethylene plant.

15. The method for operating as claimed in claim 14, wherein the additive composition is added at a temperature range varying from about 60° C. to about 180° C.

16. A method for reducing fouling and polymer deposits in a primary fractionator by controlling and inhibiting polymerization of pyrolysis gasoline in the primary fractionator, wherein the method comprises a step of treating the pyrolysis gasoline with the additive composition as claimed in claim 1.

17. A method to extend a run-length of a primary fractionator or of an ethylene plant by reducing fouling and polymer deposits in the primary fractionator by controlling and inhibiting polymerization of pyrolysis gasoline in the primary fractionator or an ethylene plant, wherein the method comprises a step of treating the pyrolysis gasoline with the additive composition as claimed in claim 1.

* * * * *